US008123786B2

(12) United States Patent
Lins

(10) Patent No.: US 8,123,786 B2
(45) Date of Patent: Feb. 28, 2012

(54) PEDICLE-BASED FACET JOINT FIXATION SYSTEMS AND METHODS

(75) Inventor: Robert E. Lins, Boca Raton, FL (US)

(73) Assignee: US Spine, Inc., Salt Lake City, UT (US)

( * ) Notice: Subject to any disclaimer, the term of this patent is extended or adjusted under 35 U.S.C. 154(b) by 598 days.

(21) Appl. No.: 12/257,951

(22) Filed: Oct. 24, 2008

(65) Prior Publication Data

US 2009/0112264 A1 Apr. 30, 2009

Related U.S. Application Data

(60) Provisional application No. 60/982,266, filed on Oct. 24, 2007, provisional application No. 60/984,261, filed on Oct. 31, 2007, provisional application No. 60/987,258, filed on Nov. 12, 2007.

(51) Int. Cl.
*A61B 17/88* (2006.01)
(52) U.S. Cl. .................................. 606/279; 606/247
(58) Field of Classification Search .................. 606/247, 606/250–278, 279, 246, 248, 249, 105
See application file for complete search history.

(56) References Cited

U.S. PATENT DOCUMENTS

| | | | | |
|---|---|---|---|---|
| 5,102,412 A * | 4/1992 | Rogozinski | ............... | 606/86 A |
| 5,116,334 A * | 5/1992 | Cozad et al. | ............... | 606/250 |
| 5,380,326 A * | 1/1995 | Lin | ............... | 606/330 |
| 5,415,659 A * | 5/1995 | Lee et al. | ............... | 606/276 |
| 5,540,688 A * | 7/1996 | Navas | ............... | 606/266 |
| 5,989,251 A * | 11/1999 | Nichols | ............... | 606/250 |
| 6,063,089 A * | 5/2000 | Errico et al. | ............... | 606/278 |
| 6,077,263 A * | 6/2000 | Ameil et al. | ............... | 606/276 |
| 6,387,097 B1 * | 5/2002 | Alby | ............... | 606/277 |
| 6,860,884 B2 * | 3/2005 | Shirado et al. | ............... | 606/330 |
| 7,011,659 B2 * | 3/2006 | Lewis et al. | ............... | 606/276 |
| 7,967,845 B2 * | 6/2011 | Lauryssen et al. | ............... | 606/250 |
| 2002/0169451 A1 * | 11/2002 | Yeh | ............... | 606/61 |
| 2004/0087948 A1 | 5/2004 | Suddaby | | |
| 2006/0036243 A1 * | 2/2006 | Sasso et al. | ............... | 606/61 |
| 2008/0058808 A1 * | 3/2008 | Klyce et al. | ............... | 606/61 |
| 2008/0103512 A1 * | 5/2008 | Gately | ............... | 606/151 |

* cited by examiner

*Primary Examiner* — Eduardo C Robert
*Assistant Examiner* — Jan Christopher Merene
(74) *Attorney, Agent, or Firm* — Stoel Rives, LLP; Matthew D. Thayne

(57) ABSTRACT

The present disclosure provides pedicle-based facet fixation systems and methods. The pedicle-based construct utilized includes a pedicle screw, pedicle anchor, or the like that is selectively secured to a pedicle of a spine of a patient. The pedicle-based construct is selectively coupled to one end of a rod or other elongate member. The other end of the rod or other elongate member is selectively coupled to a clamping mechanism. This clamping mechanism is selectively secured to a facet joint of the spine of the patient, engaging one or both of the associated superior facet and inferior facet. In operation, the pedicle-based construct, rod or other elongate member, and clamping mechanism securely grasp and compress the facet joint, thereby fixing it.

15 Claims, 12 Drawing Sheets

PEDICLE-BASED FACET JOINT FIXATION SYSTEMS AND METHODS

CROSS-REFERENCE TO RELATED APPLICATION(S)

The present non-provisional patent application claims the benefit of priority of U.S. Provisional Patent Application Ser. No. 60/982,266, filed on Oct. 24, 2007, and entitled "SPINAL PLATE-INTERBODY DEVICE CONSTRUCT;" U.S. Provisional Patent Application Ser. No. 60/984,261, filed on Oct. 31, 2007, and entitled "SPINAL PLATE-INTERBODY DEVICE CONSTRUCT;" and U.S. Provisional Patent Application Ser. No. 60/987,258, filed on Nov. 12, 2007, and entitled "SPINAL PLATE-INTERBODY DEVICE CONSTRUCT;" the contents of all of which are incorporated in full by reference herein.

FIELD OF THE INVENTION

The present invention relates generally to surgically-implantable spinal devices. More specifically, the present invention relates to pedicle-based construct facet joint fixation systems and methods configured to be implanted in a spine of a patient via an open or minimally-invasive surgical (MIS) procedure to provide facet joint fixation through a pedicle-based construct, e.g., a pedicle screw, pedicle anchor, or the like, coupled to a rod or elongated member with a clamping mechanism engaged to the facet joint.

BACKGROUND OF THE INVENTION

In the treatment of various spinal ailments/defects, it is often desirable to stabilize/immobilize one or more facet joints of the spine of a patient, either via an open or MIS procedure. Bone arthrodesis or fusion is a procedure used to assist in the stabilization/immobilization and healing of impaired bones or joints. In particular, facet arthrodesis is used to fuse a facet joint including a superior facet and an inferior facet in spinal treatment operations. There are numerous conventional implants, devices, systems, instruments, and associated methods for performing such stabilization/immobilization procedures via numerous approaches. For example, conventional systems and methods can include bone screws that are screwed or bored through the superior and inferior facets to immobilize the facet joint so as to permit the adjoined bone sections to fuse together. Wire has also been used to loop around the facets to immobilize the facet joint.

Disadvantageously, these conventional systems and methods require drilling or boring of the facet joint. Additionally, these systems and methods can loosen over time. What is still needed in the art, however, is an improved implant, device, system, instrument, and associated methods for performing such stabilization/immobilization procedures that may be effectively utilized in only a few relatively simple steps, making it essentially foolproof for a surgeon employing it.

BRIEF SUMMARY OF THE INVENTION

In various exemplary embodiments, the present invention provides pedicle-based facet fixation systems and methods. The pedicle-based construct utilized includes a pedicle screw, pedicle anchor, or the like that is selectively secured to a pedicle of a spine of a patient. The pedicle-based construct is selectively coupled to one end of a rod or other elongate member. The other end of the rod or other elongate member is selectively coupled to a clamping mechanism. This clamping mechanism is selectively secured to a facet joint of the spine of the patient, engaging one or both of the associated superior facet and inferior facet. In operation, the pedicle-based construct, rod or other elongate member, and clamping mechanism securely grasp and compress the facet joint, thereby fixing it.

In an exemplary embodiment of the present invention, a pedicle-based facet fixation system includes a pedicle-based construct selectively affixed to a pedicle of a spine of a patient; a rod selectively coupled to the pedicle-based construct; and a clamping mechanism selectively coupled to the rod, wherein the clamping mechanism is selectively affixed to a facet joint of the patient to provide compression forces and fixation on the facet joint including an inferior facet and a superior facet. The pedicle-based construct can include a pedicle screw operable to engage a bony structure, wherein the pedicle screw includes a screw head; and a tulip engaged to the screw head, wherein the tulip includes an opening; wherein the rod includes a ball secured within the tulip and wherein the rod extends out of the opening. Optionally, the pedicle-based construct further includes a rotatable hinge coupling the tulip to the pedicle screw. The clamping mechanism can include a first clamp member fixedly coupled to the rod; and a second clamp member selectively slidingly coupled to the rod. Each of the first clamp member and the second clamp member includes a plurality of angled teeth to engage one of the inferior facet and the superior facet. Optionally, the first clamp member is configured to engage the inferior facet; and the second clamp member is configured to distract to engage the superior facet. The pedicle-based facet fixation system can further include a securing mechanism to lock the second clamp member in place in a desired location to provide compression of the facet joint. Optionally, the pedicle-based facet fixation system further includes a distraction device operable to distract the second clamp to engage the facet joint. Movement of an upper portion of the pedicle-based construct translates into compression forces anchoring across the inferior facet resulting in fixation of the facet joint. The pedicle-based facet fixation system provides facet joint fixation without screw fixation across the facet joint. Optionally, the pedicle-based facet fixation system is inserted through a minimally invasion surgical procedure. Alternatively, the rod includes a hump portion operable to provide clearance of the facet joint. The rod can include a first section; a second section selectively rotatable from the first section; and a mechanism to secure the first section and the second section in position.

In another exemplary embodiment of the present invention, a pedicle screw facet fixation system includes a pedicle screw including a tulip, wherein the pedicle screw is selectively affixed to a pedicle of a spine of a patient; a rod selectively coupled to the tulip; a first clamp member fixedly coupled to the rod and operable to selectively engage an inferior facet, wherein movement of the tulip translates into compression forces anchoring across the inferior facet resulting in fixation of the facet joint; and a mechanism to secure the rod to the tulip. The pedicle screw facet fixation system can further include a second clamp member slidingly coupled to the rod and operable to engage a superior facet associated with the inferior facet; and a mechanism to secure the second clamp member in place on the rod. The pedicle-based facet fixation system provides facet joint fixation without screw fixation across the facet joint. Optionally, the pedicle-based facet fixation system is inserted through a minimally invasion surgical procedure.

In yet another exemplary embodiment of the present invention, a pedicle-based facet fixation method includes securing a pedicle-based construct to a bony structure; positioning a rod within the pedicle-based construct; engaging the rod to an inferior facet through a fixed clamp coupled to the rod; and securing the pedicle-based construct to lock the rod in a position to provide compression force on the inferior facet for facet fixation. The pedicle-based facet fixation method can further include distracting a sliding clamp coupled to the rod to a superior facet associated with the inferior facet; and locking the sliding clamp in a desired position.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

In various exemplary embodiments, the present invention provides pedicle-based facet fixation systems and methods. The pedicle-based construct utilized includes a pedicle screw, pedicle anchor, or the like that is selectively secured to a pedicle of a spine of a patient. The pedicle-based construct is selectively coupled to one end of a rod or other elongate member. The other end of the rod or other elongate member is selectively coupled to a clamping mechanism. This clamping mechanism is selectively secured to a facet joint of the spine of the patient, engaging one or both of the associated superior facet and inferior facet. In operation, the pedicle-based construct, rod or other elongate member, and clamping mechanism securely grasp and compress the facet joint, thereby fixing it. Advantageously, the present invention provides facet joint fixation with the requirement to drill or bore the facet joint, and the present invention provides a facet fixation mechanism that does not loosen over time as much as conventional mechanisms.

Figure 1:
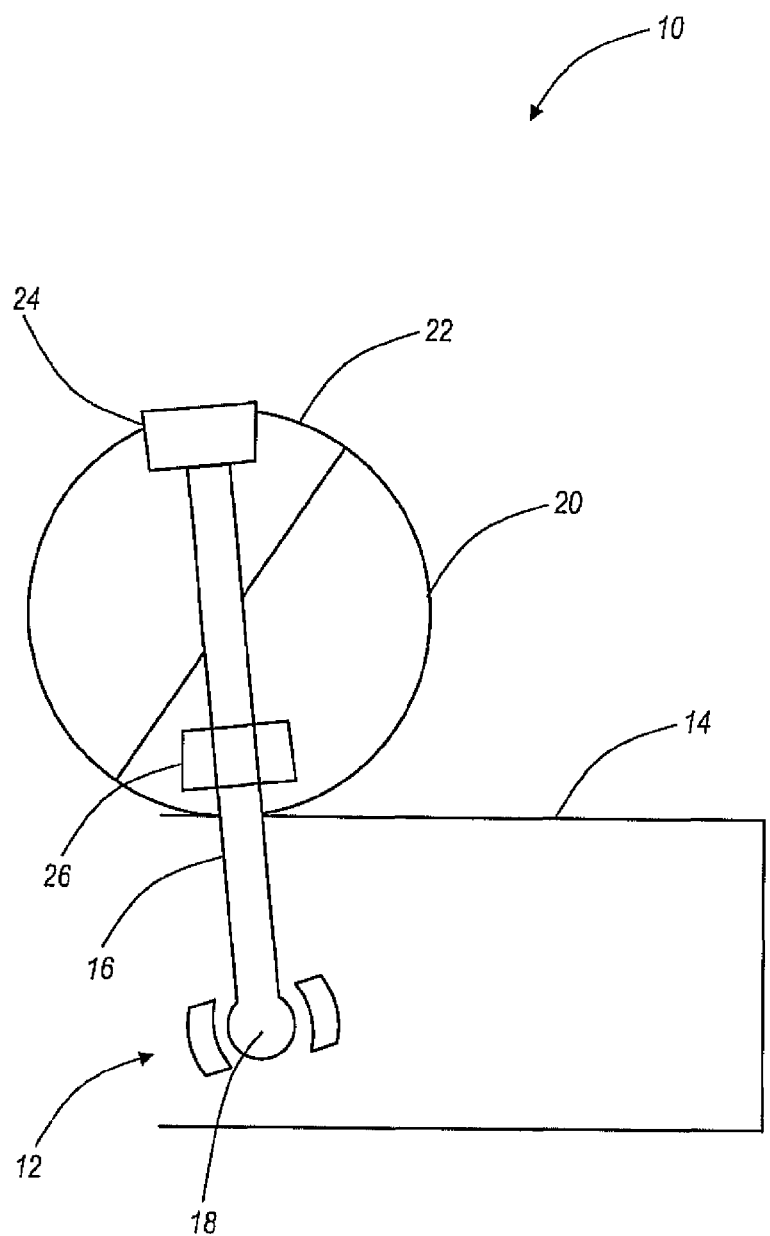
FIG. 1 illustrates a pedicle-based facet fixation system according to an exemplary embodiment of the present invention.

Referring to FIG. 1, a pedicle-based facet fixation system 10 is illustrated according to an exemplary embodiment of the present invention. The pedicle-based facet fixation system 10 includes a pedicle-based construct 12, such as a pedicle screw, pedicle anchor, or the like, selectively secured to transverse processes 14 or the like. The pedicle-based construct 12 is selectively coupled to a rod 16 or other elongated member through a ball 18 or the like disposed to one end of the rod 16. The rod 16 extends from the transverse process 14 over a superior facet 20 to an inferior facet 22. For example, the rod 16 can be positioned to extend from the pedicle-based construct 12 to the facets 20, 22, and an anchoring device disposed to the pedicle-based construct 12 can be utilized to fixedly secure the rod 16 through the ball 18.

The rod 16 is selectively coupled to a clamping mechanism that can include a first clamp 24 and a second clamp 26. The first clamp 24 is configured to selectively engage the inferior facet 22, and the second clamp 26 is configured to selectively engage the superior facet 20. As the pedicle-based construct 12 is secured to the transverse processes 14, the rod 16 is configured to translate compression force to the clamps 24, 26 to provide fixation of a facet joint associated with the facets 20, 22. Specifically, the rod 16 is initially movably affixed to the pedicle-based construct 12. The rod 16 is positioned to contact the facets 20, 22. The pedicle-based construct 12 is secured to the transverse processes 14 at an angle, for example, relative to the rod 16. The rod 16 is then secured to the pedicle-based construct 12, thereby applying compression force through the rod 16 from the pedicle-based construct 12 to the clamps 24, 26.

Figure 2:
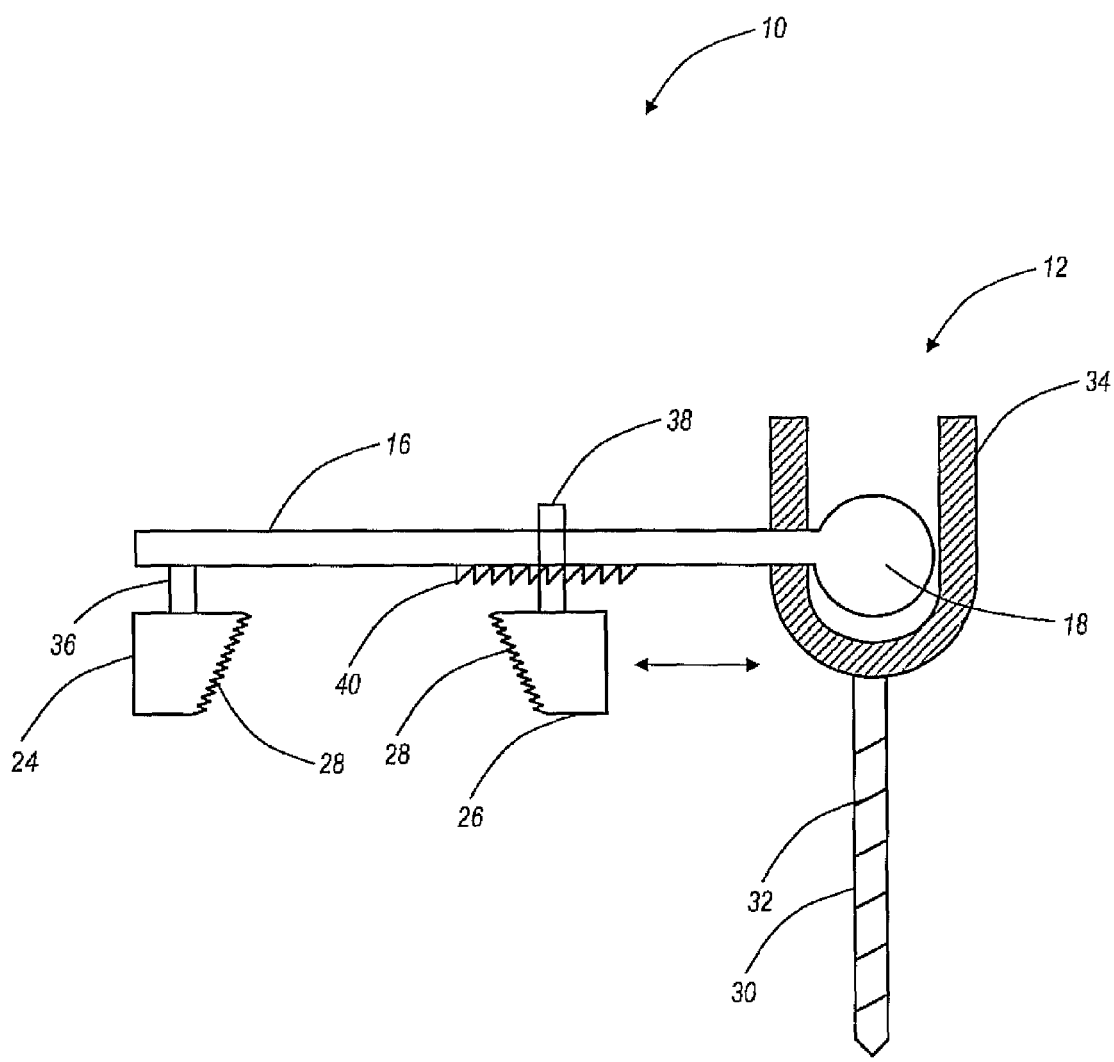
FIG. 2 illustrates another view of the pedicle-based facet fixation system of FIG. 1 according to an exemplary embodiment of the present invention.

Referring to FIG. 2, another view of the pedicle-based facet fixation system 10 is illustrated according to an exemplary embodiment of the present invention. FIG. 2 illustrates a side view of the pedicle-based construct 12 in relation to the rod 16 and the clamps 24, 26. In an exemplary embodiment, the pedicle-based construct 12 can include a pedicle screw 30 that includes a plurality of threads 32 that screw into the transverse process 14 or the like. The pedicle screw 30 can include a screw head (not shown) selectively secured to a tulip 34. The tulip 34 is a U-shaped member with a hollow interior section dimensioned to receive the ball 18. Additionally, the tulip 34 includes an opening through which the rod 16 extends from the ball 18. The tulip 34 is illustrated in a cross-sectional view with the ball 18 rotatably disposed within the tulip 34. The tulip 34 can include various mechanisms (not shown) as are known in the art to selectively secure the ball 18 to the pedicle screw 30, thereby fixing a relative position of the rod 16.

The first clamp 24 is illustrated fixedly coupled to the rod 16 through a rod 36. The second clamp 26 is slidingly coupled to the rod 16 through a rod 38. The second clamp 26 can be selectively coupled to the rod 16 through a ratchet mechanism, serrations 40, or the like on the rod 16. For example, the second clamp 26 can distract relative to the pedicle-based construct 12 and the first clamp 24 to provide compression on the facets 20, 22. Each of the clamps 24, 26 can include a plurality of angled teeth 28 which are operable to engage and grip the respective facet 20, 22.

To provide compression/fixation, the pedicle head screw is tilted inferiorly and secured to the tulip 34 to compress the inferior facet 22 by applying a compression force through the rod 16 to the first clamp 24. The various components, i.e., the pedicle screw 30, the rod 16, the ball 18, and the clamp 24, are secured in a desired position to translate force from the pedicle screw 30 to the clamp 24, thereby compressing the inferior facet 22.

Additionally, the second clamp 26 can engage the superior facet 20 and distract relative to the pedicle-based construct 12 to provide a compression force on the superior facet 20. Accordingly, in the secured position, rotation, agulation, translation, movement, etc. of the tulip 34 causes grasping, compression forces, etc. across the inferior facet 22 to provide compression/fixation of the associated facet joint. Advantageously, the pedicle-based facet fixation system 10 provides facet fixation without utilizing a screw through the facets 20, 22. The pedicle-based facet fixation system 10 can be implanted into a recipient through minimally invasive surgery (MIS), through a tubular approach, or the like.

Figure 3A:
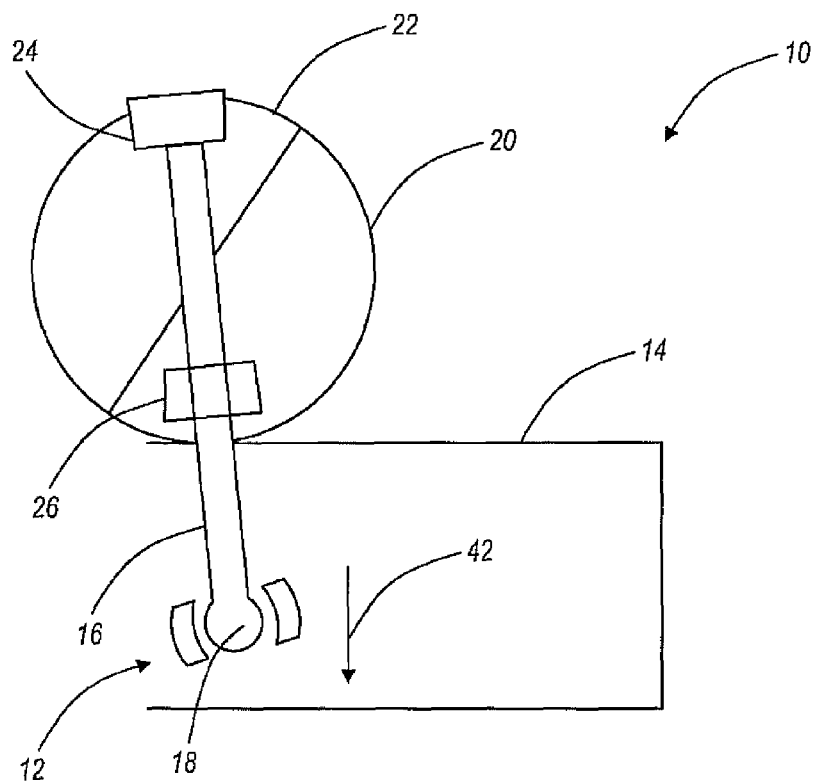
FIGS. 3a and 3b illustrate the pedicle-based facet fixation system of FIG. 1 in operation according to an exemplary embodiment of the present invention.
Figure 3B:
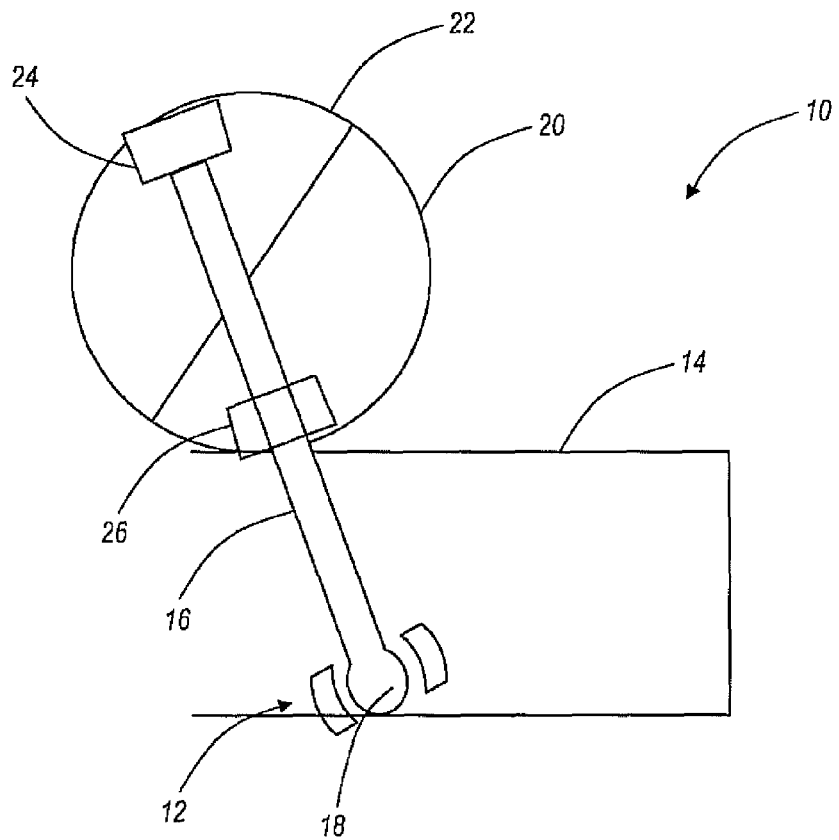

Referring to FIGS. 3a and 3b, the pedicle-based facet fixation system 10 is illustrated in operation according to an exemplary embodiment of the present invention. First, the pedicle-based construct 12 is coupled to the rod 16 or other elongated member. In FIG. 3a, the clamp 24 is positioned on the inferior facet 22 of the above vertebral body relative to the transverse processes 14. The teeth 28 grip the inferior facet 22, and the clamp 24 is secured through the positioning of the rod 16 relative to the inferior facet 22.

Additionally, the clamp 26 can be positioned on the superior facet 20 with the teeth 28 gripping the facet 20. The clamp 24 is fixedly coupled to the rod 16, and the clamp 26 is slidingly coupled to the rod 16. Accordingly, the clamp 24 can be positioned on the inferior facet 22, and the clamp 26 can be slid to engage the superior facet 20 once the clamp 24 is engaged. Once in a desired position, the clamp 26 can be secured through the serrations 40, for example.

The pedicle-based construct 12 is secured to the transverse processes 14. For example, the pedicle-based construct 12 can include a pedicle screw drilled or bored into the transverse processes 14. The pedicle-based construct 12 includes a holding mechanism to engage the ball 18 that is attached or disposed to the rod 16. For example, the holding mechanism can include the tulip 34.

Once the rod 16 is engaged to the pedicle-based construct 12, e.g., through the ball 18 and the tulip 34, the top of the pedicle-based construct 12 is positioned in a direction 42 to cause engagement of the clamp 24 with the inferior facet 22. The clamp 26 can be engaged to the superior facet 20 by distracting the clamp 26 on the rod 16. Accordingly, this positioning causes compression from the pedicle-based construct 12 to the inferior facet 22.

FIG. 3b illustrates an engaged position of the pedicle-based facet fixation system 10. Here, the pedicle-based construct 12 has been rotated, translated, angulated, or the like inferiorly in the transverse processes 14 to provide facet fixation. Accordingly, a cap, screw, top, or the like can be added to the pedicle-based construct 12 to lock the pedicle-based facet fixation system 10 in the angulated, translated position. For example, if the pedicle-based construct 12 includes a pedicle screw 30 with the tulip 34, then the pedicle-based construct 12 can include a tightening mechanism as is known in the art to secure the pedicle screw 30 in place while maintaining the angulated, translated position of the rod 16.

Figure 4A:
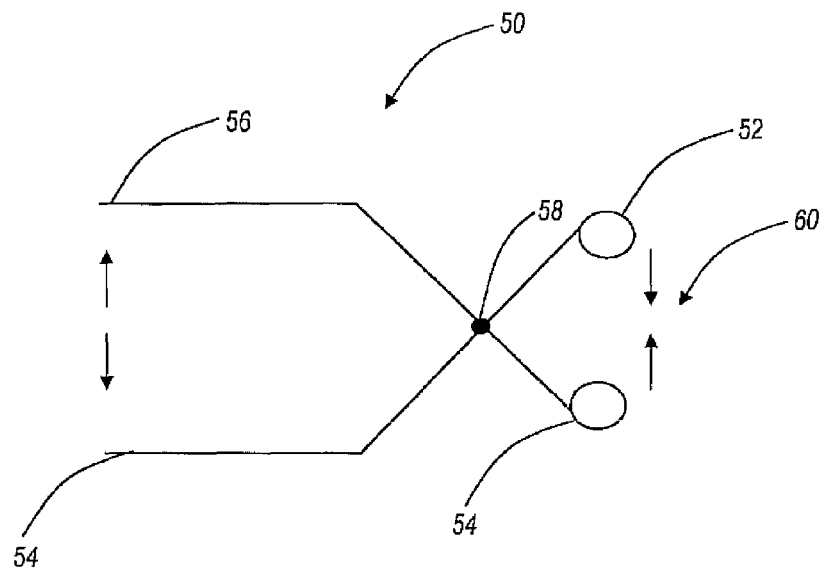
FIGS. 4a and 4b illustrate a distraction device for use with the pedicle-based facet fixation system of FIG. 1 according to an exemplary embodiment of the present invention.
Figure 4B:
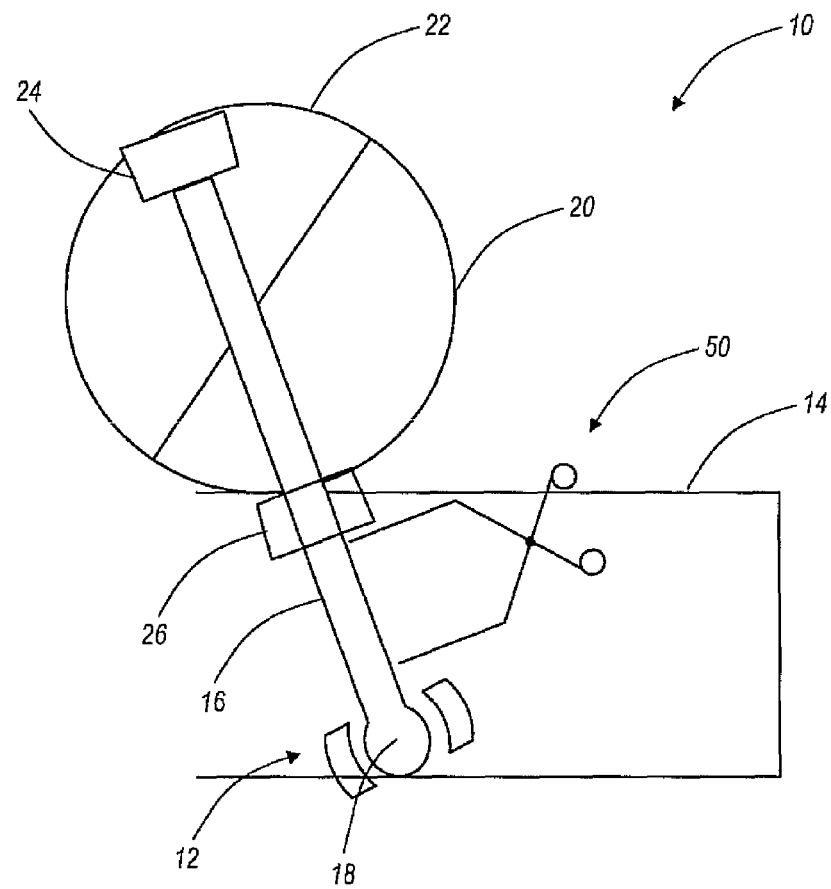

Referring to FIGS. 4a and 4b, a distraction device 50 is illustrated for use with the pedicle-based facet fixation system 10 according to an exemplary embodiment of the present invention. The distraction device 50 is operable to cause the clamp 26 to distract to the superior facet 20 and to position the clamp 26 along the rod 16 in an appropriate location. The distraction device 50 includes a first and second handle portion 52, 54 connected to a first and second end portion 56, 58 through a hinge 58. A surgeon can grip the handle portions 52, 54 to provide a force 60 to cause the end portions 56, 58 to distract.

FIG. 4b illustrates the distraction device 50 in operation with the pedicle-based facet fixation system 10. The first end 54 is positioned relative to the pedicle-based construct 12 and tie second end 56 is positioned against the second clamp 26. The surgeon can then cause the end portions 56, 58 to distract to engage the superior facet 20 and to compress the facet joint (i.e., facets 20, 22). Note, the first clamp 24 is fixedly engaged to the rod 16, and therefore a compression force applied by the distraction device 50 translates to compression of the facets 20, 22 in between the clamps 24, 26.

Figure 5:
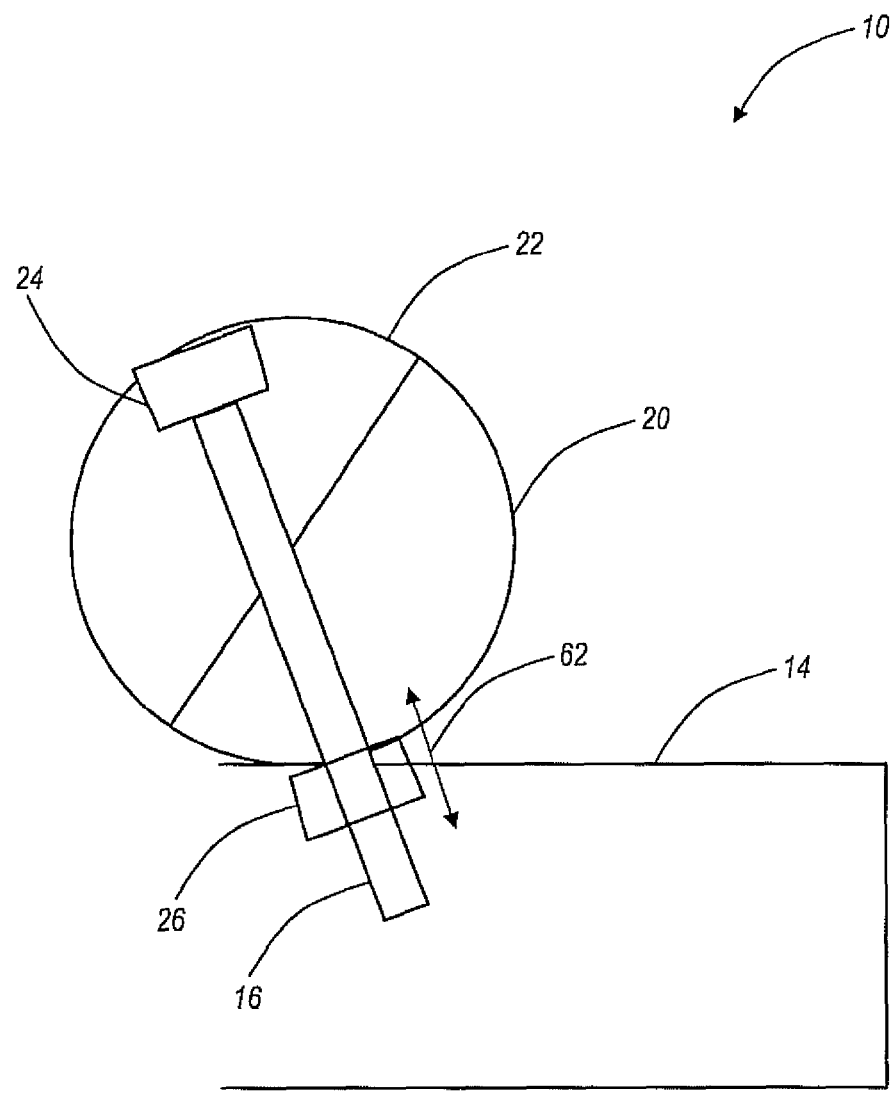
FIG. 5 illustrates an operation of the slidingly engaged clamp on the pedicle-based facet fixation system of FIG. 1 according to an exemplary embodiment of the present invention.

Referring to FIG. 5, an operation of the slidingly coupled clamp 26 on the pedicle-based facet fixation system 10 is illustrated according to an exemplary embodiment of the present invention. Here, the clamp 26 is configured to move along a direction 62 on the rod 16 or elongated member. For example, the distraction device 50 of FIGS. 4a and 4b could be utilized to engage and move the clamp 26. In addition to movement along the rod 16, the clamp 26 can also be secured in place in a desired position on the rod 16. For example, the rod 16 can include serrations, scoring, or the like to hold the clamp 26 in place in the desired position to cause compression against the facet joint.

Figure 6:
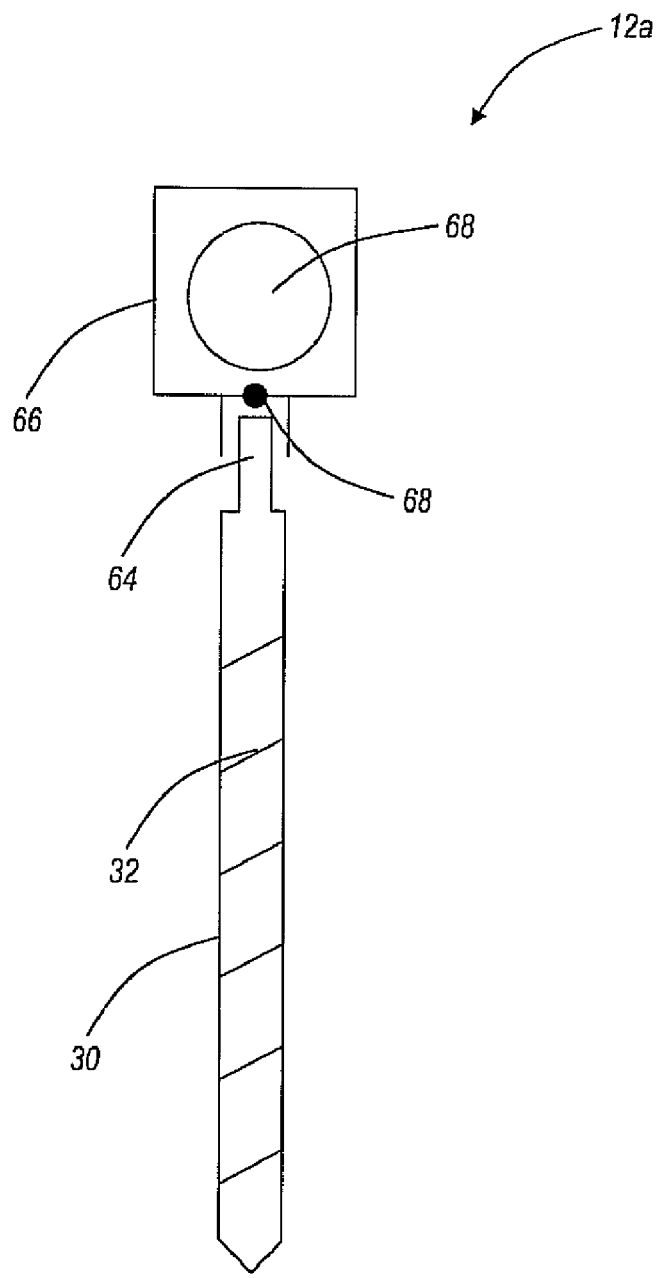
FIG. 6 illustrates a pedicle-based construct utilizing a ball in a box mechanism according to an exemplary embodiment of the present invention.

Referring to FIG. 6, a pedicle-based construct 12a is illustrated utilizing a ball in a box mechanism according to an exemplary embodiment of the present invention. The pedicle-based construct 12a includes the pedicle screw 30 with the plurality of threads 32 for engaging a bony structure (e.g., the transverse processes 14). The pedicle screw 30 includes a head portion 64 operable to engage a box 66, such as through a rotating hinge 68, through a weld, an interference fit, or the like. The box 66 includes an opening 70 dimensioned to fit the rod 16, and through which the rod 16 can extend. Additionally, the interior of the box 66 can include the ball 18. For example, the ball 18 and the rod 16 can be placed within the box 66 prior to implantation.

Figure 7:
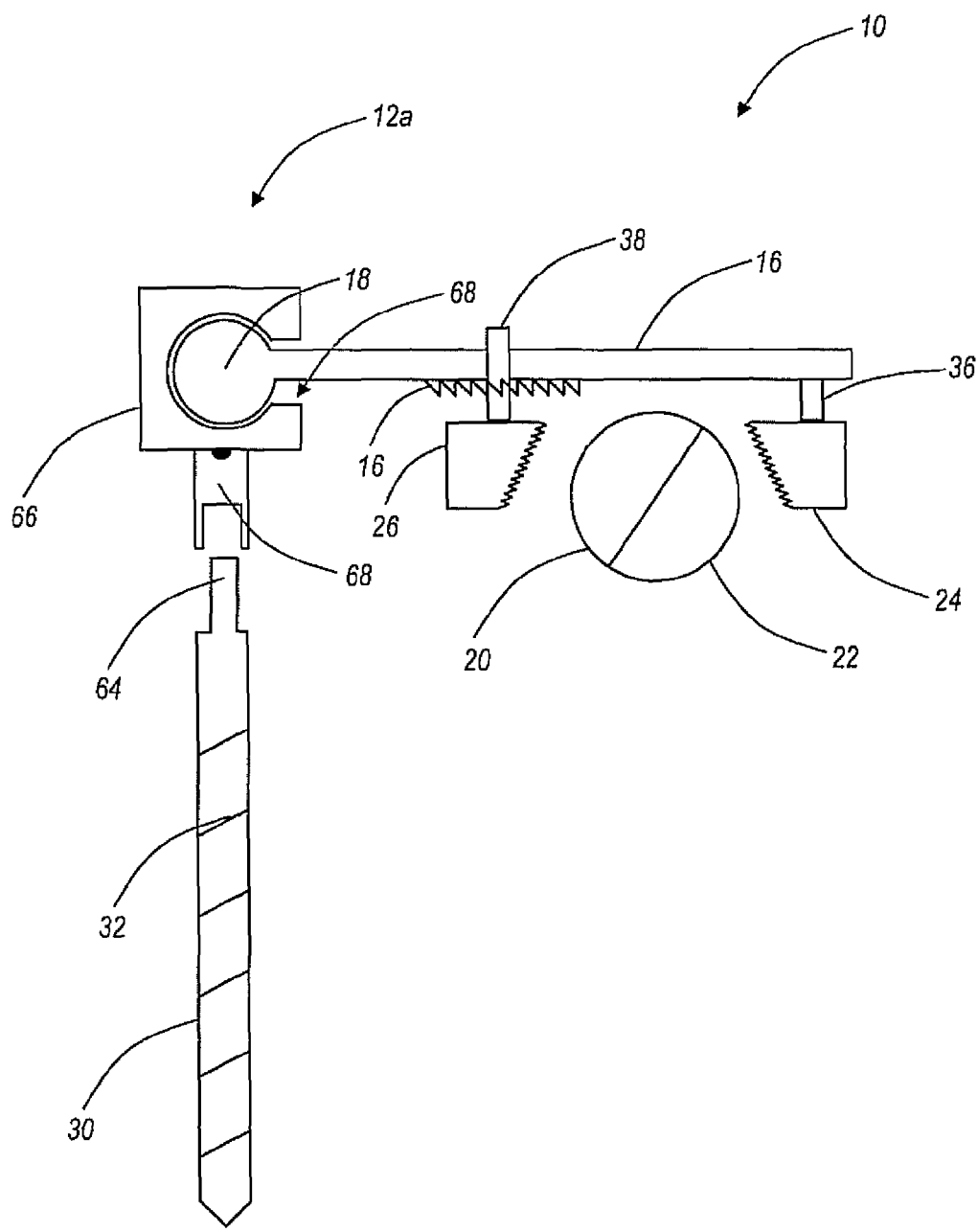
FIG. 7 illustrates the pedicle-based facet fixation system with the pedicle-based construct of FIG. 6 according to an exemplary embodiment of the present invention.

Referring to FIG. 7, the pedicle-based facet fixation system 10 is illustrated with the pedicle-based construct 12a according to an exemplary embodiment of the present invention. FIG. 7 illustrates the ball 18 disposed to the rod 16 engaged in the box 66. The pedicle screw 30 is operable to screw into a bony structure, e.g., the transverse processes 14 or the like, and to connect to the box 66, such as through the hinge 68. The ball 18 extends out from the box 66 to the rod 16. The rod 16 includes the clamps 24, 26 with the clamp 24 fixedly coupled to the rod 16 and the clamp 26 slidingly coupled to the rod 16, such as through the serrations 16.

The clamp 26 is operable to slidingly engage the superior facet 20 to compress the superior facet 20 to the inferior facet 22 to provide fixation, thereby providing a wedge. Specifically, the inferior facet 22 engages the clamp 24 which is fixed along the rod 16. The clamp 26 is moved to a desired position along the rod 16 to engage the superior facet 20 for a desired amount of compression. Once positioned, the clamp 26 can be fixed to the rod 16.

Figure 8:
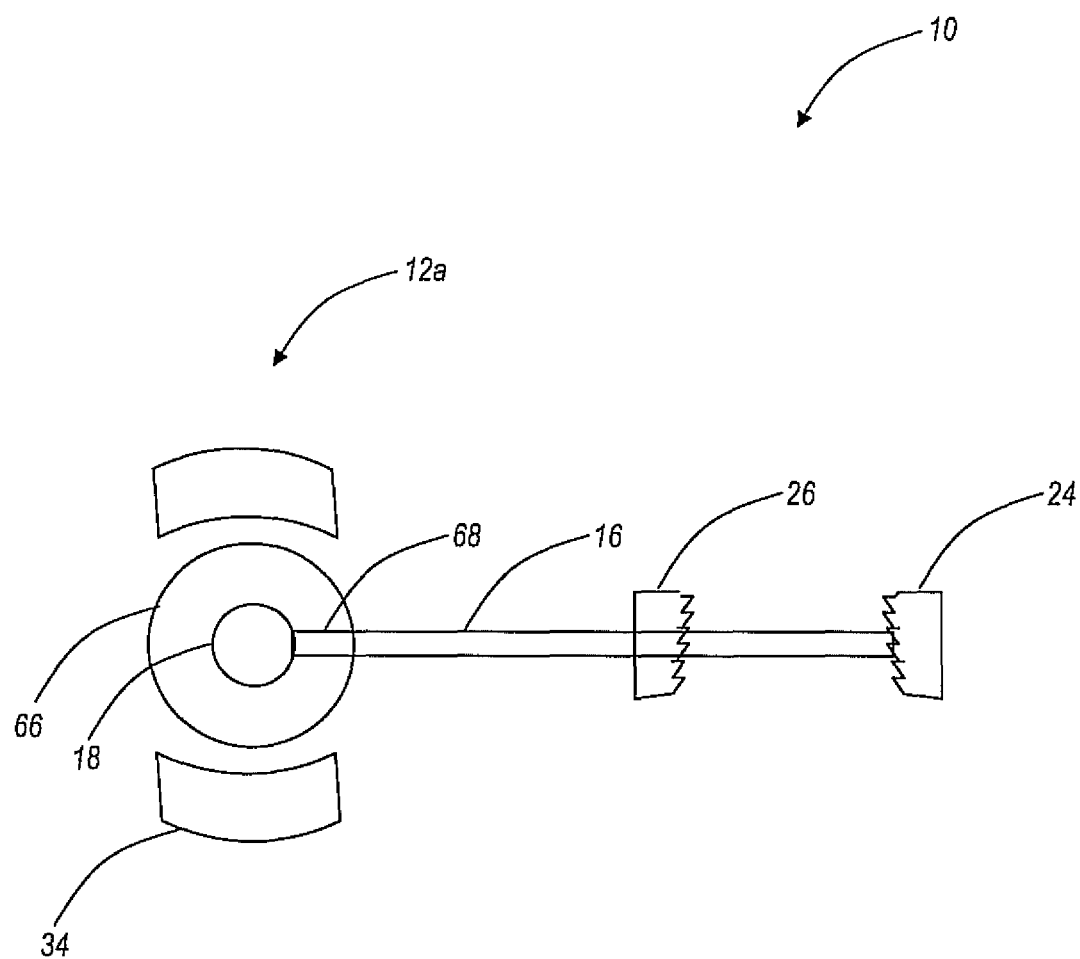
FIG. 8 illustrates another view of the pedicle-based facet fixation system with the pedicle-based construct of FIG. 6 according to an exemplary embodiment of the present invention.

Referring to FIG. 8, another view is illustrated of the pedicle-based facet fixation system 10 with the pedicle-based construct 12a according to an exemplary embodiment of the present invention. In FIG. 8, the box 66 is illustrates as a sphere enclosed in the tulip 34.

Figure 9A:
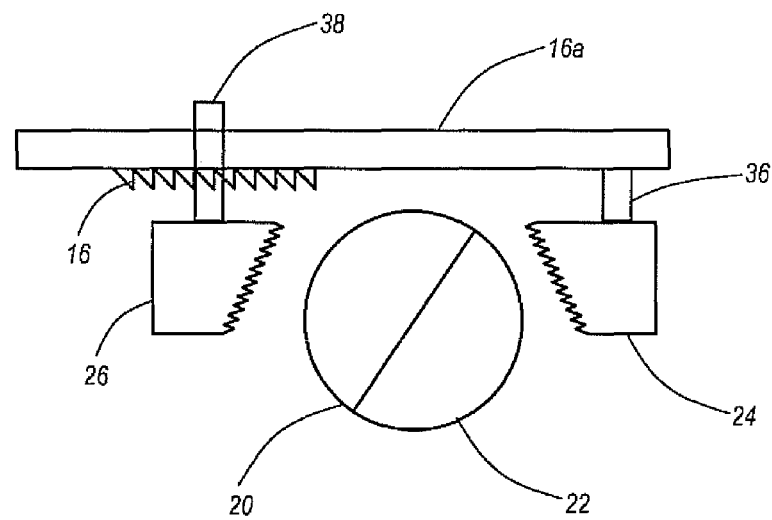
FIGS. 9a and 9b illustrate embodiments of different rods for the pedicle-based facet fixation system according to an exemplary embodiment of the present invention.
Figure 9B:
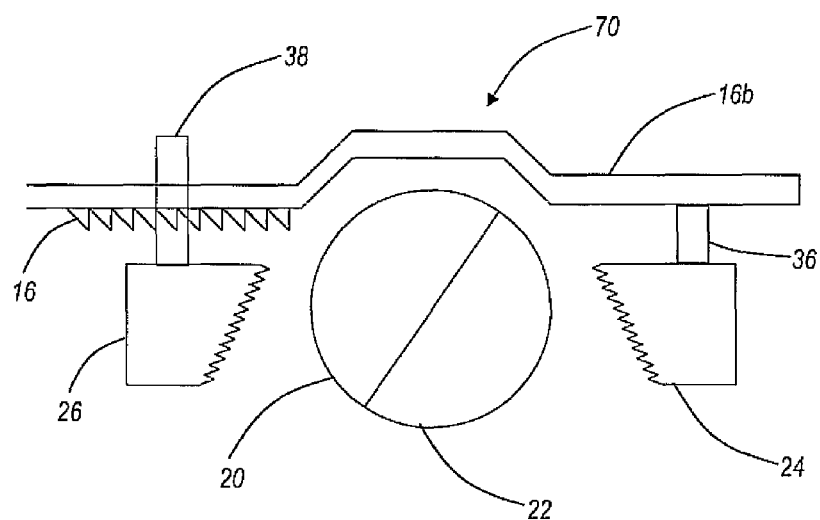

Referring to FIGS. 9a and 9b, embodiments are illustrated of different rods 16a, 16b for the pedicle-based facet fixation system 10 according to an exemplary embodiment of the present invention. The rod 16a (FIG. 9a) can be substantially straight extending from the ball 18 (not shown) to the clamp 24. Alternatively, the rod 16b (FIG. 9b) can include a hump shape 70 in a middle portion of the rod 16. Specifically, the hump shape 70 can be located between the rods 36, 38 which hold the clamps 24, 26 to allow clearance of the facets 20, 22. The hump shape 70 provides clearance for the facets 20, 22.

Figure 10A:
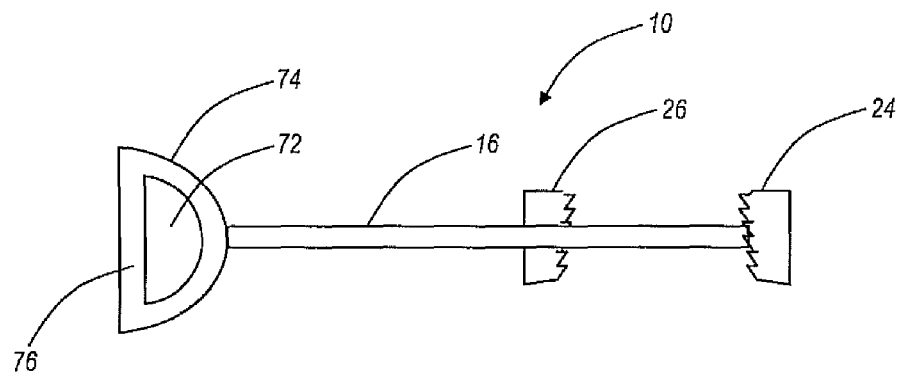
FIGS. 10a and 10b illustrate the pedicle-based facet fixation system with a pedicle screw and an opening in the rod for engaging a tulip according to an exemplary embodiment of the present invention.
Figure 10B:
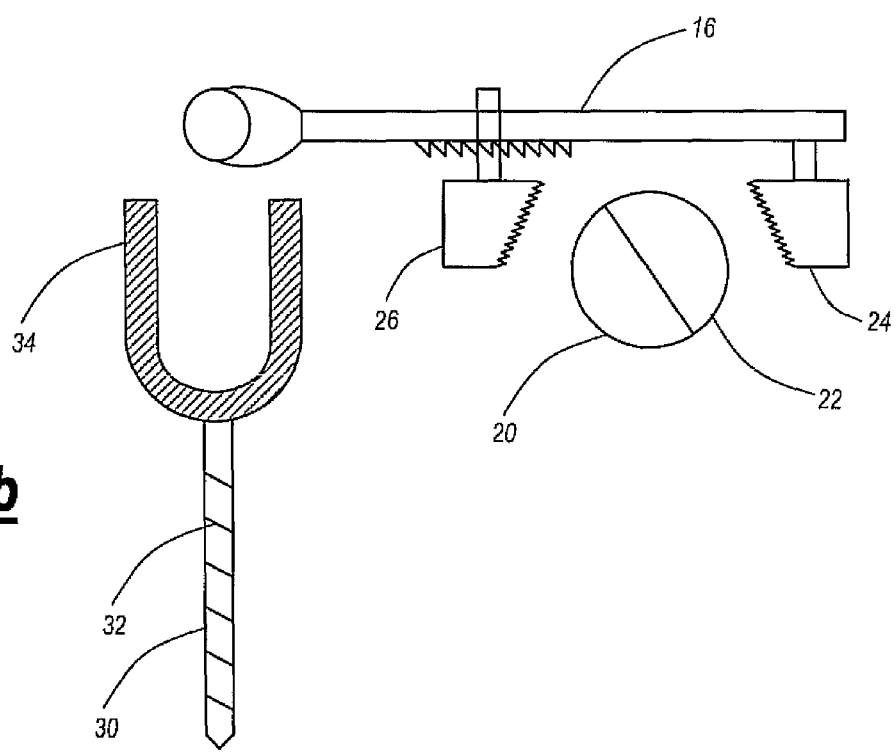

Referring to FIGS. 10a and 10b, the pedicle-based facet fixation system 10 is illustrated with the pedicle screw 30 and an opening 72 in the rod 16 for engaging the tulip 34 according to an exemplary embodiment of the present invention. Here, the rod 16 extends to an end portion 74 which encompasses the opening 72 and terminates at a ball portion 76. The opening 72 is dimensioned to fit over a portion of the tulip 34 which is secured by the pedicle screw 30. Accordingly, the rod 16 is secured to the pedicle screw 30 through placing the opening 72 over the tulip 34 and subsequently securing the tulip 34 to a bony structure through various mechanisms as are known in the art.

Figure 11:
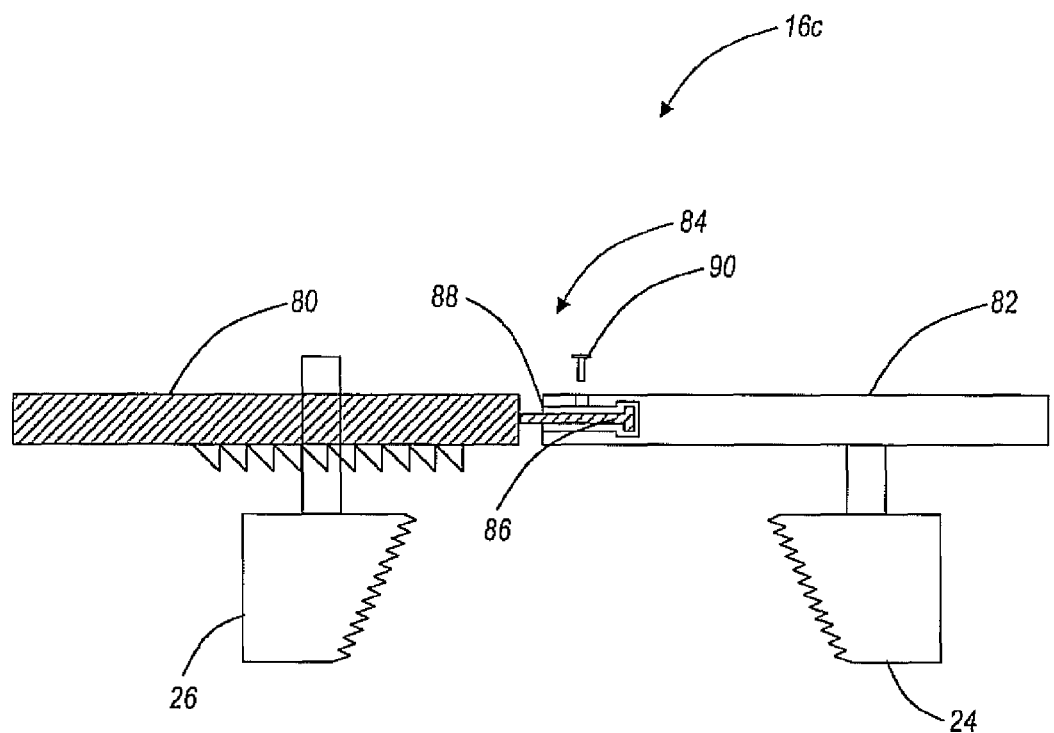
FIG. 11 illustrates another embodiment of a rod for the pedicle-based facet fixation system according to an exemplary embodiment of the present invention.

Referring to FIG. 11, another embodiment of a rod 16c is illustrated for the pedicle-based facet fixation system 10 according to an exemplary embodiment of the present invention. The rod 16c includes a mechanism to allow the clamps 24, 26 to rotate independently from one another. Specifically, the rod 16c includes two sections 80, 82 with each of the clamps 24, 26 engaged to one of the sections 80, 82. The sections 80, 82 are interconnected at a midpoint 84. For example, the section 80 can include an extension portion 86 which fits within an open portion 88 of the section 82. Accordingly, the sections 80, 82 can rotate independently of one another to enable the clamps 24, 26 to properly engage the facets 20, 22, e.g. at different angles along the rod 16c. Once engaged to the facets 20, 22, the rod 16c can be fixed through a screw 90, for example, that can be inserted into the section 82 to the extension portion 86 to prevent further rotation of the sections 80, 82.

Figure 12:
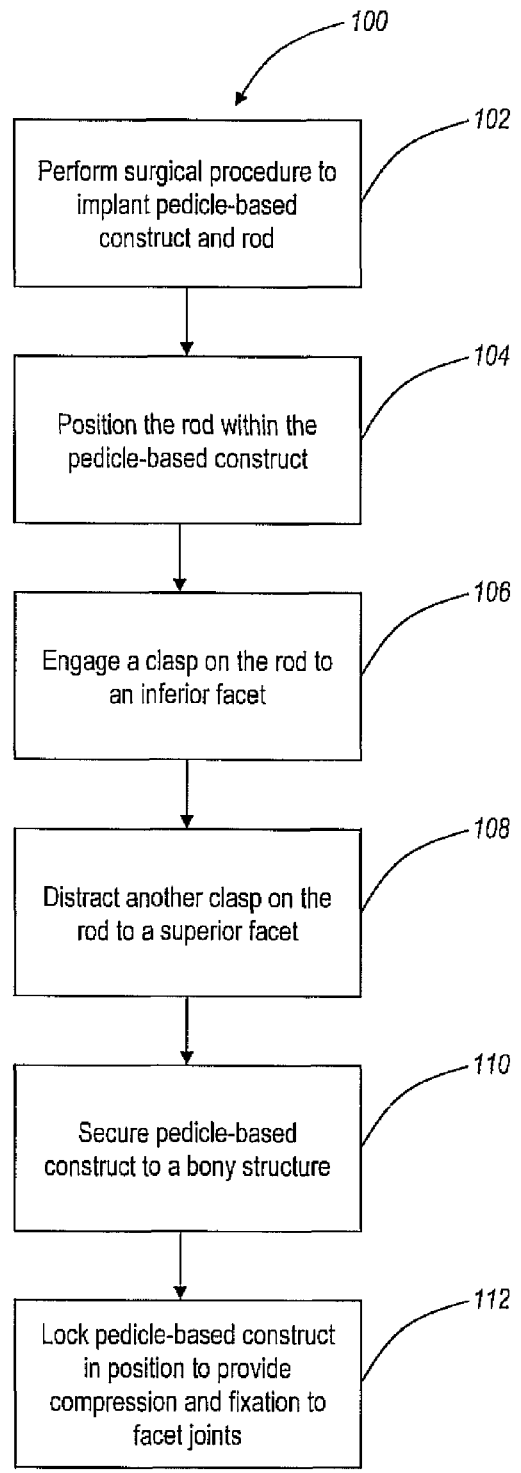
FIG. 12 illustrates a flowchart of a pedicle-based facet fixation mechanism according to an exemplary embodiment of the present invention.

Referring to FIG. 12, a flowchart illustrates a pedicle-based facet fixation mechanism 100 according to an exemplary embodiment of the present invention. The pedicle screw based facet fixation mechanism 100 starts by performing a surgical procedure (e.g., MIS, etc.) to implant a pedicle-based construct and rod into a receiving patient (step 102). The rod is positioned within the pedicle-based construct (step 104). Also, the rod is extended to an above facet joint including an inferior and a superior facet. A clamp on the rod is engaged to the inferior facet (step 106). Another clamp on the rod is distracted to the superior facet to provide a compression force on the facet joint for facet fixation (step 108). The pedicle-based construct is secured to a bony structure (e.g., the transverse processes or the like) (step 110). Finally, the pedicle-based construct is locked in position to provide compression and fixation of the facet joints (step 112).

As described herein, the pedicle-based facet fixation system utilizes rotation/angulation/translation/movement of an upper portion/top/tulip of a pedicle screw or pedicle-based construct to cause grasping/compressive forces/contact anchoring across the above inferior facet for resulting compression/fixation of the facet joint. The system can utilize additional compression from separate/different grasp/grip/clamp/contact with the superior facet. An end of the clamp/clamp rod construct sits against an inside/top of the pedicle screw or pedicle-based construct. The shape of the end may be circular/octagonal/or any shape that allows it to stay in contact with the pedicle screw or pedicle-based construct when the top of the construct is rotated/angulated/translated. Advantageously, fixation across facet joint is provided without screw fixation across the facet joint. The system may be placed through a hole, expandable retractor, or open approach.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A pedicle-based facet fixation method, comprising:
   securing a pedicle-based construct comprising a pedicle screw to a pedicle of a spine of a patient;
   positioning a rod within the pedicle-based construct;
   engaging the rod to a first facet through a fixed clamp coupled to the rod; and
   securing the pedicle-based construct relative to the fixed clamp to lock the rod in a position to provide compression force on the first facet for facet fixation.

2. The pedicle-based facet fixation method of claim 1, further comprising:
   distracting a sliding clamp coupled to the rod to a second facet associated with the first facet; and
   locking the sliding clamp in a desired position.

3. The pedicle-based facet fixation method of claim 2, wherein the first facet comprises an inferior facet and wherein the second facet comprises a superior facet.

4. The pedicle-based facet fixation method of claim 2, wherein at least one of the sliding claim and the fixed clamp comprises a plurality of teeth for gripping a facet.

5. The pedicle-based facet fixation method of claim 2, wherein the step of locking the sliding clamp in a desired position comprises using at least one of a ratchet mechanism and a plurality of serrations to prevent the sliding clamp from moving away from the locking clamp.

6. The pedicle-based facet fixation method of claim 1, wherein the method is performing without placing a screw through any of the patient's facets.

7. The pedicle-based facet fixation method of claim 1, wherein the pedicle-based construct further comprises a tulip.

8. The pedicle-based facet fixation method of claim 7, wherein the step of positioning a rod within the pedicle-based construct tulip comprises positioning a portion of the rod within the tulip.

9. The pedicle-based facet fixation method of claim 8, wherein the step of positioning a rod within the pedicle-based construct tulip comprises positioning a ball positioned on the rod within the tulip.

10. The pedicle-based facet fixation method of claim 1, wherein the rod comprises a hump portion operable to provide clearance of the facet joint.

11. The pedicle-based facet fixation method of claim 1, further comprising the step of approximating a second clamp with the fixed clamp to provide compression on a facet joint positioned between the first facet and a corresponding second facet.

12. The pedicle-based facet fixation method of claim 11, further comprising the step of rotating the second clamp with respect to the fixed clamp.

13. The pedicle-based facet fixation method of claim 12, wherein the rod comprises:
   a first section; and
   a second section selectively rotatable with respect to the first section.

14. The pedicle-based facet fixation method of claim 13, wherein the rod further comprises a mechanism to secure the first section and the second section in position such that the first section cannot rotate with respect to the second section.

15. The pedicle-based facet fixation method of claim 11, wherein the second clamp comprises a sliding clamp.

\* \* \* \* \*